:::
United States Patent
Leleve

(12) United States Patent
(10) Patent No.: US 6,765,353 B2
(45) Date of Patent: Jul. 20, 2004

(54) METHOD AND APPARATUS FOR DETECTING THE STATE OF HUMIDITY ON A ROAD ON WHICH A VEHICLE IS TRAVELLING

(75) Inventor: Joël Leleve, Bobigny Cedex (FR)

(73) Assignee: Valeo Vision, Bobigny Cedex (FR)

( * ) Notice: Subject to any disclaimer, the term of this patent is extended or adjusted under 35 U.S.C. 154(b) by 0 days.

(21) Appl. No.: 10/183,310

(22) Filed: Jun. 25, 2002

(65) Prior Publication Data

US 2003/0001509 A1 Jan. 2, 2003

(30) Foreign Application Priority Data

Jun. 29, 2001 (FR) .............................................. 01 08903

(51) Int. Cl.[7] .............................. B60Q 1/00; B60Q 1/02
(52) U.S. Cl. ............................. 315/77; 315/82; 362/465
(58) Field of Search ...................... 315/77, 82; 362/465, 362/464, 466, 467, 276; 340/469, 459, 462, 437, 468, 936

(56) References Cited

U.S. PATENT DOCUMENTS 6,049,171 A * 4/2000 Stam et al. ................... 315/82
6,254,259 B1 * 7/2001 Kobayashi ................... 362/465
6,281,632 B1 * 8/2001 Stam et al. ................... 315/82

FOREIGN PATENT DOCUMENTS

| DE | 41 33 359 A | 4/1993 |
| DE | 198 54 964 A | 6/2000 |
| EP | 0 642 950 A | 3/1995 |
| FR | 2 707 390 A | 1/1995 |
| FR | 2 721 400 A1 | 12/1995 |

* cited by examiner

Primary Examiner—Don Wong
Assistant Examiner—Chuc Tran
(74) Attorney, Agent, or Firm—Morgan & Finnegan, LLP

(57) ABSTRACT

A vehicle travels along a road with its lights on because of the conditions outside the vehicle. It has an onboard optical sensor associated with the headlights and arranged to form an image of a zone of the road in front of the vehicle, so that the state of humidity of the road can be determined, and the light output modified accordingly. The zone concerned, on the road, consists of at least one segment oriented in the direction of travel, so that the image created by the optical sensor is a characteristic curve representing the light distribution on the road. This image is compared with a reference curve to determine the state of humidity. The reference curve represents light distribution when the road is dry.

13 Claims, 2 Drawing Sheets

METHOD AND APPARATUS FOR DETECTING THE STATE OF HUMIDITY ON A ROAD ON WHICH A VEHICLE IS TRAVELLING

FIELD OF THE INVENTION

This invention relates to a method for detecting the state of humidity on a road, on which a motor vehicle is travelling under conditions of obscurity such that the lighting system of the vehicle is in use, the lighting system including, in particular, at least one driving light or headlight. The invention equally relates to apparatus carried on the vehicle for detecting the said state of humidity.

BACKGROUND OF THE INVENTION

In the development of automotive lighting systems, a major modification is concerned with lighting in bad weather, and in particular the provision of a "bad weather headlight". This is a dipped beam headlight which is arranged to give several levels of light distribution in accordance with the state of humidity or dampness on the road in front of the vehicle. It is also arranged to reduce the emission of light directed towards vehicles travelling in the opposite direction, and an increase in light intensity on one or both verges of the road.

U.S. Pat. No. 6,049,171 (U.S. Pat. No. 6,049,171) provides an onboard optical sensor in the vehicle, and a means for forming on this sensor an image of a zone of the road situated in front of the vehicle. If at least one vehicle is detected in this zone, the light intensity of the headlight is reduced. Humidity sensors are also provided to prevent excessive reflection of light emission from the headlights being reflected towards the driver. However, humidity sensors will detect rain drops on the windshield, but they do not permit the state of humidity of the road and/or of the atmosphere to be analysed.

In addition, it is known from French published patent specification FR 2 721 400A to provide a method and apparatus for detecting fog or smoke, for a motor vehicle, which comprises a camera mounted in the vehicle together with means for analysing the contrast of the points in the image. However, the state of humidity of the road and/or the atmosphere is not detected by this apparatus.

DISCUSSION OF THE INVENTION

A main object of the invention is to provide a method for evaluating with accuracy the state of humidity of a road, with a view in particular to choosing the level of adjustment of a bad weather headlight. In such a headlight, the various levels of light distribution which are provided as a function of the road correspond to various states, which may for example be defined as follows:

a slightly damp road, a very muddy road, an intermediate state between the two foregoing states, and rain.

In no way is it conceivable to envisage control of the headlight by simple visual appreciation on the part of the driver. The driver's perception of the environment is too subjective, and it is imperative to arrange that the system will operate automatically on the basis of a method and apparatus which are adapted accordingly.

An object of the invention is therefore to provide such a method and apparatus which will give a reliable evaluation of the state of humidity on the road, and/or that of the atmosphere, while being relatively simple and inexpensive.

According to the invention in a first aspect, a method of detecting the state of humidity on a road on which a motor vehicle is driving under conditions of obscurity necessitating the use of the vehicle lighting system, there being an optical sensor fitted in the vehicle, the method including the steps of forming on the optical sensor an image of a zone of the road in front of the vehicle, is characterised in that the said zone of the road consists of at least one segment which is oriented in the direction of travel of the vehicle, whereby the image is a characteristic profile, in the form of a line or curve, representing the distribution of light on the road; the said image is compared with a reference in order to determine the state of humidity; and the said reference is the characteristic said curve, for the light distribution in at least one equivalent segment of dry road.

It is of course possible to rotate the optical sensor through 90° and to associate with it a processing of the signal, for example by a digital signal processor, in order to achieve the same level of information.

Experience has shown that with the solution provided by the invention, the profile of the characteristic curve of the light distribution for a dry road (the reference characteristic) with that for a slightly damp or slightly humid road, intersect at a crossover point which is situated at a certain distance in front of the vehicle. The light distribution on the damp road is stronger than on the dry road closer to the vehicle than this crossover point, but becomes weaker than on a dry road at distances beyond the crossover point.

Preferably, the length of the road segment under surveillance is sufficient to cause a crossover point to be defined by the said characteristic profiles corresponding to a damp road and a dry road. This length may be about 15 meters from the headlight.

Preferably, the or each image of the zone under surveillance on the road, formed on the optical sensor, is scanned in a direction defined in a vertical plane parallel to the direction of travel of the vehicle. The profile of the light distribution characteristic on a segment of road is obtained by this scanning of the elements of the optical sensor.

According to the invention in a second aspect, apparatus for detecting the state of humidity of a road on which a motor vehicle is travelling under conditions of obscurity such that the vehicle lighting system, including at least one driving light, is in use, the apparatus comprising an optical sensor carried in the vehicle, and imaging means for forming on the optical sensor an image of a zone of the road in front of the vehicle, is characterised in that the imaging means is adapted to form an image of at least one segment of the said zone, oriented in the direction of travel of the vehicle, whereby the image concerned is a profile, in the form of a line or curve, characteristic of the light distribution on the road, in that a reference, consisting of the characteristic profile, in the form of a line or curve, for at least one segment of dry road is stored in a memory means of the apparatus, and in that the apparatus further includes a comparison means for comparing the image received by the optical sensor with the said reference.

Preferably, the optical sensor consists of a CCD strip, or a battery of photodiodes, or a CCD camera, or an MOS camera.

Preferably also, photosensitive cells which constitute the elementary points or pixels of the optical sensor are scanned in a vertical direction, of a direction defined in a vertical plane parallel to the direction of travel.

The headlights (or driving lights) of the vehicle may be systematically oriented in the correct direction with respect to the ground, in particular by means of an automatic attitude correcting device. The characteristic curve for the segment which serves for reference purposes may be generated when the road is dry and then stored in a memory.

The apparatus of the invention quantifies the humidity levels on the road.

Preferably, the optical sensor consists of a camera having an angular field (in particular of the order of 60°), sufficient to render it unnecessary to adjust the orientation of the camera with respect to the ground. In this connection, such an angular field enables variations in inclination of the vehicle with respect to the ground, which are generally less than 10°, to be absorbed.

However, it is preferable that the optical sensor consists of a camera installed in a said driving light and subjected to the same automatic attitude correction as the driving light, which is systematically oriented in the correct direction with respect to the ground by automatic correction apparatus.

Further features and advantages of the invention will appear more clearly on a reading of the following detailed description of a preferred embodiment of the invention, which is given by way of non-limiting example only and with reference to the accompanying drawings.

DESCRIPTION OF A PREFERRED EMBODIMENT OF THE INVENTION

Figure 1:
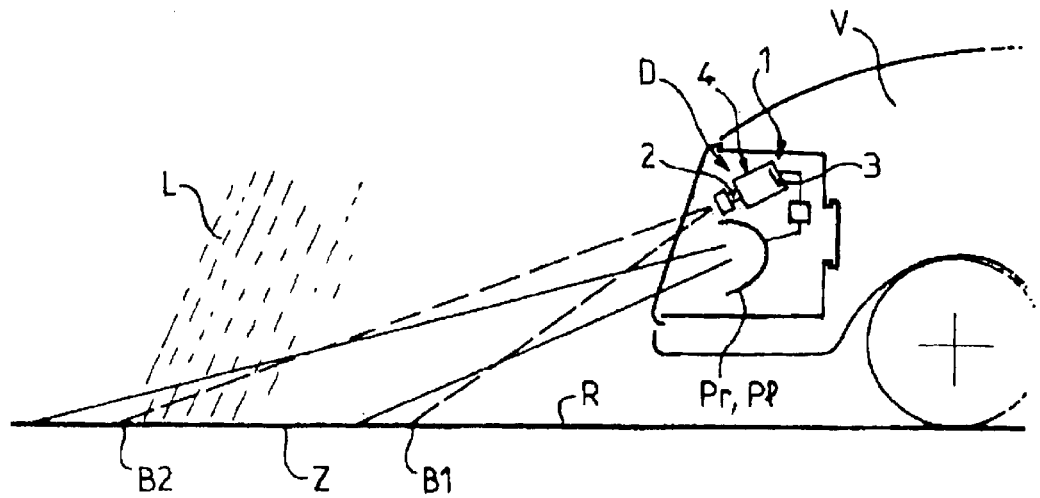
FIG. 1 is a diagram of an apparatus for detecting the state of humidity on a road, in accordance with the invention.
Figure 3:
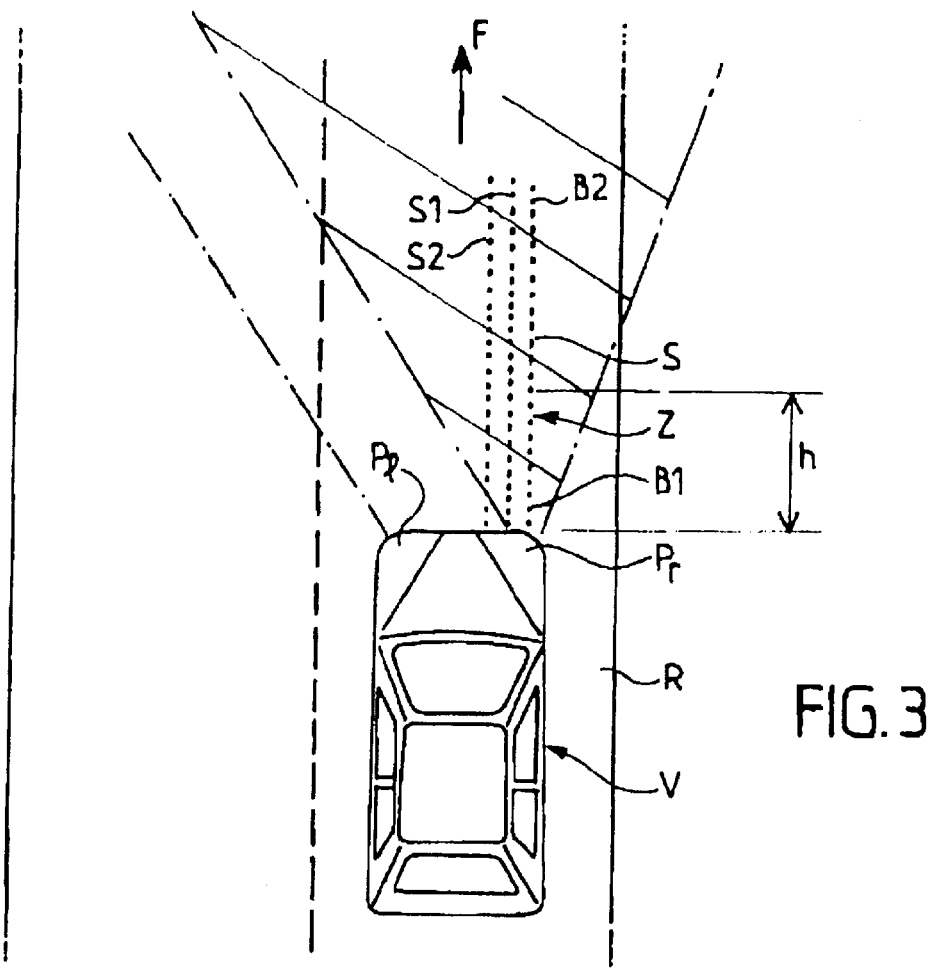
FIG. 3 is a diagrammatic top plan view of a vehicle in motion, equipped with a humidity detecting apparatus according to the invention.

With reference to the drawings, and particularly FIGS. 1 and 3, a motor vehicle V drives along a road R under darkness or other conditions of obscurity such that the vehicle lighting system, and in particular the front headlights Pr, Pl, are in use.

A detector D for detecting the state of humidity of the road R is arranged to control the intensity of the light emission from the headlights P, in response to the humidity on the road itself and the form of the road. The apparatus D comprises an optical sensor 1 which is fitted on the vehicle, together with an imaging means 2 for forming on the sensor 1 an image of a zone Z of the road in front of the vehicle.

Figure 2:
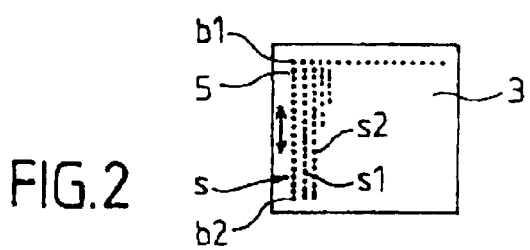
FIG. 2 is a diagrammatic scrap view showing a matrix of elementary points or pixels in an optical sensor, in particular in a CCD camera.

The sensor 1 is arranged to work in visible light. It is of an inexpensive type currently available commercially. The sensor 1 may consist of a CCD strip (or load transfer system), while the imaging means 2 consists of at least one lens. The optical sensor 1 preferably comprises the receiver plate 3 (FIG. 2) of a CCD camera 4, with the lens 2 being the objective of the same camera.

The receiver plate 3 consists of a matrix of photosensitive cells which constitute elementary points or pixels 5. The camera is so oriented that the zone Z under surveillance corresponds substantially to the zone being illuminated by the headlights P when they are working in a dipped beam mode.

It will of course be understood that the camera 4, instead of being a CCD camera, may be of some different type, for example an MOS type.

The image which is received, which is analysed as to its level of relative luminosity, is that of at least one segment S (see FIG. 3) of the road which is oriented in the direction of travel F of the vehicle. The image of this segment S is formed in the vertical segment s of the plate 3, FIG. 2.

Scanning of the pixels of the plate 3 is performed in columns as indicated by an arrow, that is to say in a vertical plane parallel to the direction of travel F. One pixel of the matrix 3 on the image s corresponds to one point on the segment S on the road. Thus, the endmost pixel b1 in the segment s in FIG. 2 corresponds to the point B1 of the segment S situated closest to the vehicle in FIG. 3. The lower pixel b2 in the segment s in FIG. 2 corresponds to the point B2 on the road shown in FIG. 3, in a segment further away from the vehicle. A level of relative luminosity (or light level) supplied by the corresponding pixel of the image s may be associated with each point on the road situated at a different distance ahead of the vehicle.

Figure 4:
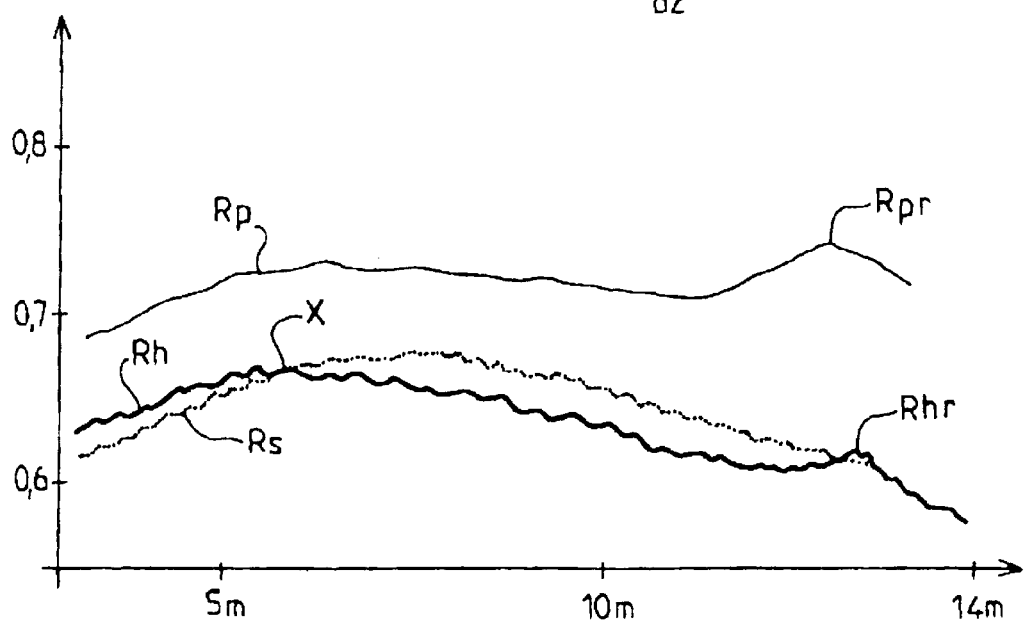
FIG. 4 is a diagram of the characteristic curves of the light level relating to a segment of road, when damp, when dry, and in the rain.

In this way, the diagram of FIG. 4 can be constructed, which shows on the ordinate the relative luminosity level detected by a pixel in the segment s (FIG. 2), while the abscissa shows the distance h in FIG. 3 of the headlight from the corresponding point on the road. In FIG. 4, the curve Rs corresponds to a dry road, with for example a dry asphalt surface. The curve Rh corresponds to a humid or damp road in which the asphalt is damp, for example after a shower of rain or in very light rain. Finally, the curve Rp corresponds to conditions of heavy rain.

The curve Rs can be seen to have a shape which is generally convex upwards, the maximum value of relative luminosity level being obtained for points on the road situated at a distance between 5 and 10 meters from the headlight in this example.

The damp road curve Rh starts above the dry road curve Rs, but then crosses the latter at a crossover point X, corresponding to a point on the road which, in this example, lies about 6 meters ahead of the headlights. The curve Rh then passes below the curve Rs. Beyond a distance of about 12 or 13 meters, the curve Rh rises again at Rhr to form a small peak, the summit of which is slightly above the curve Rs.

The curve Rp, representing heavy rain L (FIG. 1) lies generally above both of the other two curves in FIG. 4. It has a convex portion with a maximum situated at a distance of about 6 or 7 meters from the headlights. This curve Rp shows a fairly pronounced peak Rpr at a distance from the headlights which is substantially the same as the distance corresponding to the peak Rhr.

Intermediate states, not shown, corresponding to curves between the ones shown in FIG. 4 can of course be evaluated if desired.

The curves in FIG. 4, resulting from experimental measurements, illustrate the capacity of the apparatus to discern the state of the road and the presence of rain. Thus, in the presence of rain, the signal Rp transmitted by the photosensitive cells of the matrix 3 is the sum of the reflection on the ground and on the rain drops intercepted by the light beam from the headlights. The amplitude of the signal and its noise level characterise this state.

In the absence of rain, but where the road is still damp, the ground produces greater diffusion and is more specular than in the dry state. It is found that beyond 5 meters, and more precisely beyond the crossover point X, the signal Rh for the damp road becomes smaller than the signal Rs for the dry road. This is explained by the fact that part of the light in the light beam is reflected forward of the vehicle, which leads to a reduction in the light received by the cells 5.

In the dry state, the measured level Rs serves as a reference.

Accordingly, it will be seen that the apparatus is able to show a clear distinction between a damp road and a dry road, by comparison between the curves Rh and Rs, which display a crossover point. It is also possible to distinguish the degree of humidity of the road with intermediate curves not shown. The comparisons of the relative luminosity levels obtained may be performed in tables with respect to reference values corresponding to the results Rs.

In order to obtain correct functioning, it should be ensured that the headlights Pr, Pl are systematically oriented in the best direction. This is achieved using an automatic attitude correcting device for each headlight, which maintains the angle of inclination of the light beam from the headlight with respect to the road at a constant value, as will be explained with reference to FIG. 5.

The three curves in FIG. 4 may be obtained by weighing values measured on several parallel segments S, S1, S2 etc. on the road. One segment s, s1, s2 of the receiver plate 3, situated on a vertical scanning column, corresponds to each of the said segments. It is thus possible to determine a mean value of the relative luminosity level at a distance h from the headlight of the vehicle by calculating the mean of the relative luminosity levels at several points on the road situated at a common distance from the headlight.

Figure 5:
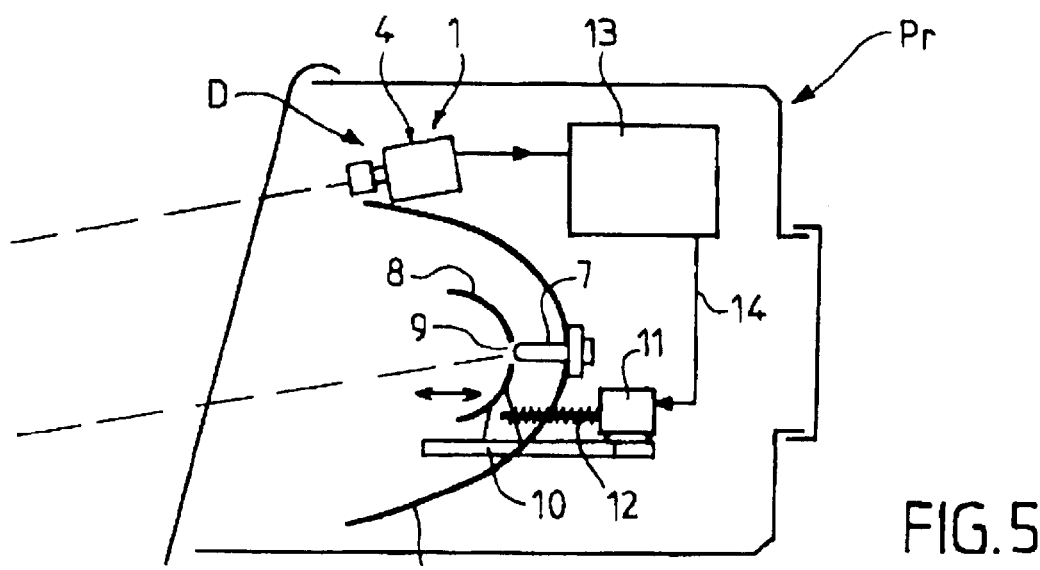
FIG. 5 is a more detailed diagram of the apparatus for detecting the state of humidity on the road.

Reference is now made to FIG. 5, which shows one example of the apparatus in more detail, though still diagrammatically. The camera 4 of the humidity detecting apparatus is mounted in the headlight Pr, and its optic is thus protected against dirt. A wiping apparatus is generally arranged for the optic of the headlight so the camera 4 benefits from it.

The reflector 6 of the headlight is systematically oriented in the best direction with respect to the ground by means of an automatic attitude correcting device (not shown), as mentioned above. The camera 4 is mounted in such a way as to follow the angular movements of the reflector 6. The lamp 7 is disposed at the centre of the reflector 6. A concave mirror 8, smaller than the reflector 6, is disposed in the concavity of the reflector 6. The mirror 8 has a central aperture 9 for the lamp 7. The mirror 8 is mounted for movement in order to modify the light beam at several levels of definition, according to the state of humidity of the road as detected by the apparatus.

It will of course be realised that other means may be used for modifying the light distribution, for example with elliptical headlights.

In the example shown here, the mirror 8 is mounted on a support 10 which can be displaced in translation by an electric motor 11 actuating a leadscrew 12. The support 10 may be mounted for sliding movement along the optical axis of the reflector 6, or it may be pivoted about a point of articulation of a pedestal supporting the motor 11.

The information supplied by the camera 4 as to the level of luminosity at different points on the road are passed to an electronic module 13 for processing the signals, which performs in suitable tables the comparison of the measured value of the luminosity levels of the points on the road with the reference Rs as explained above. This reference is stored in a memory of the processing means 13. The reference curve Rs may be generated automatically or at the initiative of the driver while travelling on a dry road.

The electronic module 13 is an image processing module of a known type. The quantity of information is high, and is such as to permit fine discrimination in the humidity conditions on the road in front of the vehicle.

According to the particular humidity condition detected, the module 13 passes on its output line 14 a control signal to the motor 11 so as to displace the moving mirror 8 by a predetermined amount such as to modify the level of definition of the light beam in response to the detected humidity. A similar control is provided for the other headlight P1.

The use of a standard camera 4, or of inexpensive CCD optical sensors, is of particular advantage. The camera could be used for other purposes, for example automatic lighting of the headlights, or detection of fog. The incorporation of the apparatus in the headlight enables benefit to be obtained of the automatic wiping facility often provided on headlight glasses, and it also protects the apparatus mechanically.

What is claimed is:

1. A method of detecting the state of humidity of a road for a vehicle, the vehicle including at least one driving light for illuminating the road ahead of the vehicle and an onboard optical sensor, the method comprising the steps, while the vehicle is moving along the road in a direction of travel, with said at least one driving light in use to direct a beam of light on a zone of the road in front of the vehicle of:

forming an image of said zone on the optical sensor, said zone comprising at least one segment oriented in the direction of travel, whereby said image is a characteristic profile representing the light distribution on the road;

establishing a reference consisting of a characteristic profile representing light distribution in at least one equivalent segment of dry road; and comparing said image with the said reference so as to determine the instant state of humidity.

2. A method according to claim 1, wherein the step of forming said image comprises selecting a length of said at least one segment sufficient for said characteristic profile, when relating to a damp road, to intersect the reference profile in a crossover point.

3. A method according to claim 1, wherein said segment length is approximately 15 meters from said at least one driving light.

4. A method according to claim 1, further comprising the step of scanning the image of said zone formed on the optical sensor in a direction lying in a vertical plane parallel to the direction of travel.

5. A method according to claim 1, wherein said zone comprises a plurality of parallel segments oriented in the direction of travel, the step of forming an image comprising forming an image consisting of vertical segments each corresponding to said segment of the zone on the road, the method further including the step of calculating the mean of the relative luminous levels at several points on the road situated at a common distance from said at least one driving light, whereby to determine a mean value of said level at said distance.

6. For a vehicle having at least one driving light, an apparatus for detecting the state of humidity on a road along which the vehicle is moving in a direction of travel, with said at least one driving light directing a beam of light on the road ahead of the vehicle, said apparatus comprising an onboard optical sensor and imaging means in front of the sensor for forming on the sensor an image of a zone of the road in front of the vehicle, said zone comprising at least one segment oriented in the direction of travel, whereby said image is a characteristic profile representing the light distribution on the road; memory means for storing a reference consisting of a characteristic profile corresponding to light distribution in at least one equivalent segment of dry road; and comparison means connected to the memory means and the optical sensor for comparing said image received by the sensor with said reference.

7. The apparatus according to claim 6, wherein the optical sensor is selected from the group consisting of a CCD strip, an array of photodiodes, a CCD camera, and an MOS camera.

8. The apparatus according to claim 7, wherein the optical sensor comprises photosensitive cells constituting the pixels of the sensor, the apparatus including means for scanning said cells in a direction lying in a vertical plane parallel to the direction of travel.

9. The apparatus according to claim 6, wherein the optical sensor is a camera defining an angular field of the order of at least 60°, whereby any necessity to adjust the orientation of the camera in relation to the ground is absent.

10. The apparatus according to claim 6, wherein the optical sensor is a camera mounted in said driving light, the driving light including automatic attitude correcting means, the apparatus including automatic correction means connected with the camera for correcting the orientation of the camera, whereby the camera and driving light are subjected to the same attitude correction.

11. The apparatus according to claim 6, further including an electronic image processing module connected to the sensor for receiving therefrom information as to the light level at different points on the road, said module being adapted to compare measured values of said levels at points on the road with said reference stored in the memory means, the apparatus further including means for modifying the level of definition of the light beam of said at least one driving light, the comparison means being connected to said level modifying means for transmitting a control signal to the latter, whereby the modifying means modifies said level of definition in response to the detected state of humidity.

12. The method of claim 1, wherein said image is a characteristic profile representing the light distribution on the road in the direction of travel.

13. The apparatus of claim 6, wherein said image is a characteristic profile representing the light distribution on the road in the direction of travel.

* * * * *

UNITED STATES PATENT AND TRADEMARK OFFICE
CERTIFICATE OF CORRECTION

PATENT NO. : 6,765,353 B2
DATED : July 20, 2004
INVENTOR(S) : Joe Leleve

It is certified that error appears in the above-identified patent and that said Letters Patent is hereby corrected as shown below:

<u>Title page,</u>
Item [56], References Cited, please insert:
-- OTHER REFERENCES
French Search Report, March 6, 2002--

<u>Column 6,</u>
Line 35, "with the said reference" should be -- with said reference --.

Signed and Sealed this

Eighth Day of March, 2005

JON W. DUDAS
*Director of the United States Patent and Trademark Office*